United States Patent [19]

Shapiro

[11] 4,343,782
[45] Aug. 10, 1982

[54] CYTOLOGICAL ASSAY PROCEDURE

[76] Inventor: Howard M. Shapiro, 238 Highland Ave., West Newton, Mass. 02165

[21] Appl. No.: 27,736

[22] Filed: Apr. 6, 1979

Related U.S. Application Data

[63] Continuation-in-part of Ser. No. 898,153, Apr. 20, 1978, abandoned.

[51] Int. Cl.$^3$ .................. G01N 1/30; G01N 13/00; G01N 21/25; G01N 33/48; G01N 33/52; G01N 33/54; G01N 33/74
[52] U.S. Cl. .................. 424/3; 23/230 R; 23/230 B; 250/302; 250/304; 356/39; 424/7; 424/8; 424/11; 424/12; 424/13
[58] Field of Search .................. 424/1, 1.5, 3, 7, 8, 424/11, 12, 13; 250/302, 304; 23/230 R, 230 B; 356/39

[56] References Cited

U.S. PATENT DOCUMENTS

| | | | |
|---|---|---|---|
| 3,545,927 | 12/1970 | Scott | 23/230 B |
| 3,710,933 | 1/1973 | Fulwyler | 356/39 X |
| 3,883,247 | 5/1975 | Adams | 356/39 |
| 3,899,297 | 8/1975 | Hirschfeld | 424/3 X |
| 3,900,558 | 8/1975 | Kinsolving | 424/12 |
| 3,916,205 | 10/1975 | Kleinerman | 250/461 |
| 3,971,952 | 7/1976 | Inbar | 250/302 X |
| 3,992,631 | 11/1976 | Harte | 250/365 |
| 4,055,799 | 10/1977 | Coster | 23/230 B X |

FOREIGN PATENT DOCUMENTS

| | | | |
|---|---|---|---|
| 1319710 | 6/1973 | United Kingdom | 356/39 |
| 1452547 | 10/1976 | United Kingdom | 424/3 |

OTHER PUBLICATIONS

Wilder, The J. of Histochem. &Cytochem., vol. 25, No. 7, 1977, pp. 888–891.
Traganos, The J. of Histochem. & Cytochem., vol. 24, No. 1, 1976, pp. 40–48.
Seligmann, J. of Cell Biol., vol. 75, No. 2, pt2, 1977, p. 103A, No. CI 1128.
Simms et al., Biochemistry, vol. 13, 1974, pp. 3315–3330.
Shapiro et al., Chem. Abs., vol.84, 1976, Ab. No. 118126h.
Traganos et al., Chem. Abs., vol. 84, 1976, Ab. No. 70515e.
Hartline, Sci., vol. 203, Mar. 9, 1979, pp. 992–994.
Edelman, Sci., vol. 192, Apr., 1976, pp. 218–226.
Kinsolving et al., J. Pharm. & Exptl. Therap. vol. 192, 1975, pp. 654–669.
Horan et al., Sci., vol. 198, No. 4313, Oct. 14, 1977, pp. 149–157.
Cohen et al., Rev. Physiol. Biochem. Pharmacol., vol. 83, 1978, pp. 36–88.
Bramhall et al., Biochem. &Biophys. Res. Commun., vol. 72, 1976, pp. 654–662.
Morgan et al., Biochem. & Biophys. Res. Commun., vol. 72, 1976, pp. 663–672.
Caswell et al., Biochem. & Biophys. Res. Commun., vol. 42, 1971, pp. 43–49.
Caswell et al., Biochem. & Biophys. Res. Commun., vol. 43, 1971, pp. 625–630.
Caswell et al., Biochem. & Biophys. Res. Commun., vol. 46, 1972, pp. 1757–1763.
Caswell et al., Biochem. & Biophys. Res. Commun., vol. 49, 1972, pp. 292–298.
Naccache et al., Sci., vol. 203, Feb. 2, 1979, pp. 461–463.
Chandler et al., The J. of Cell Biology, vol. 76, 1978, pp. 371–385 and 386–399.
Schuldiner et al., Biochemistry, vol. 14, 1975, pp. 5451–5460.
Korchak et al., Proc. Natl. Acad. Sci., U.S.A., vol. 75, Aug. 1978, pp. 3818–3822.
Horne et al., Blood, vol. 51, Apr. 1978, pp. 741–749.

*Primary Examiner*—Anna P. Fagelson
*Attorney, Agent, or Firm*—Kenway & Jenney

[57] ABSTRACT

Disclosed is a method of bioassay based on the detection of changes in the membrane potential of individual cells. A cell suspension is incubated with a solution of a substance capable of affecting the physiology of at least a subpopulation of cells in the suspension. During or after the incubation, a measurement representative of the membrane potential of individual cells is made. Comparison of these measurements with reference measurements provides information concerning: (1) the viability of the cells or a subgroup thereof after exposure to toxic substances; (2) the presence and concentration of factors or ligands in the solution which bind specifically to cell membrane receptors; (3) the presence of cells in the suspension sensitive to factors known to be present in the solution; (4) the cumulative effect of plural factors in the solution on the cells or a subpopulation thereof; and (5) comparisons among the effects on the cells of plural, chemically distinct factors. The preferred method of measuring membrane potential involves incubating the cells with a membrane-permeant, fluorescent, ionic dye which becomes distributed on opposite sides of the cell membrane as a function of membrane potential, and then assaying intracellular dye concentration by photometric measurements in a flow cytometer.

51 Claims, 9 Drawing Figures

CONTROL

GRAMICIDIN

VALINOMYCIN

CONCANAVALIN A

PHYTOHEMAGGLUTININ

T CELLS, CONTROL

T CELLS, PHA

B CELLS, CONTROL

B CELLS, PHA

CYTOLOGICAL ASSAY PROCEDURE

REFERENCE TO RELATED APPLICATIONS

This application is a continuation-in-part of copending application Ser. No. 898,153, filed Apr. 20, 1978, now abandoned.

BACKGROUND OF THE INVENTION

This invention relates to cytological assays and more particularly to a process for detecting and measuring cellular response to certain extracellular substances.

It has long been known that the interior of animal and plant cells is electrically negative with respect to the exterior. The magnitude of this potential difference is generally between 5 and 90 mV, with most of the potential being developed across the cell membrane.

Cell membrane potentials change in several ways with the physiologic state of the cell. Since the expenditure of metabolic energy is required to maintain potentials, the potential across the membrane of an injured or dying cell is decreased in magnitude. More specific changes in membrane potential occur within minutes following the interaction of cells with a wide variety of substances or ligands which bind with relatively high affinity to specific transmembrane receptors.

In relation to ligands and receptors, recent advances in cellular biology have demonstrated that a basic form of communication between the cells of multicellular living systems is effected through extracellular ligands or chemical messengers. These chemical messengers originate both from specialized tissues within the organism and from external sources. Their chemical structures and sites of action vary widely. They can have a zone of influence as small as a few hundred angstroms (e.g. the neuromuscular junction) or throughout the whole organism (blood-borne messengers such as hormones).

As a result of recent biochemical research in this area, it is now established that many of these chemical messengers interface with the cell receiving the message by selectively coupling to receptors located on the exterior of the cell. Apparently, the receptor recognizes the chemical messenger on the basis of its stereochemistry and/or the spatial distribution of its charged or chemically active groups. The ligand and receptor thus become non-covalently bonded in a "lock-and-key" relationship. As a result of binding, an intracellular biochemical or biophysical change takes place which induces the cell to begin or terminate some metabolic or physiological process. Ligands include substances such acetylcholine, epinephrine, and norepinephrine (neurotransmitters), insulin, growth hormone, and thyrotropin (hormones), histamine, antigens, proteins of the immune system or portions thereof, viruses, bacteria, certain toxins, and sperm. For many of these substances there exists a natural or synthetic antagonist, i.e., a substance which can reverse the physiological effect of its corresponding substance, or binds to receptors thereby excluding binding of the natural substance. Natural or synthetic agonists are also known. An agonist is a substance which binds to the receptor to initiate a physiological cellular response similar to that of the natural ligand. Many drugs now commonly employed in the practice of medicine are agonists or antagonists of natural ligands.

In many cases, the events which occur in cells subsequent to the binding of ligand to specific receptors can be duplicated by reacting the cells with other substances which bind to the receptors, e.g., with certain plant lectins or with antibody prepared against isolated receptors. It is also possible to initiate cell responses of this kind by the addition of agents which change membrane potential in the same direction as occurs following ligand-receptor interaction.

A rapid and reliable method of detecting and measuring the intracellular effect of a ligand-receptor interaction would have significant utility in biochemical research and diagnostic testing. Because of the diversity of receptor specificities among otherwise homogeneous cell populations, and because of the enormous number of different chemotactic agents, such a test should ideally be capable of assaying individual cells.

Various direct and indirect methods for detecting ligand-receptor interactions are known in the art. One class of methods employs radioactive or fluorescently tagged ligands. These are incubated with a cell-suspension, and after washing to remove unbound ligands, the radioactivity or fluoresence of the cell mass is assayed. The requirement for tagged ligands places severe limitations on the use of this technique. Another class of prior art detection methods utilizes the observation that ligand-receptor interactions are often accompanied by increases in intracellular deoxyribonucleic acid (DNA) synthesis. In certain systems, following the binding of ligands to receptor, e.g., after lymphocytes have been stimulated with antigen or mitogens such as phytohemagglutinin, DNA levels can be measured and then compared with the DNA level of a comparable cell mass in which no ligand-receptor interaction has occurred. The relative level of DNA provides a measure of the ligand-receptor interaction. This technique is limited in use because the DNA synthesis is generally not detectable for many hours or even days following ligand binding.

Still another class of methods for detecting certain types of ligand receptor interaction is based on changes in the "structuredness of the cytoplasmic matrix" as determined by measurement of the polarization of fluorescence of intracellular fluorescein. In order to be analyzed by such methods, cells must have the ability to produce intracellular fluorescein by enzymatic hydrolysis or fluorescein diacetate or a similar compound. These methods are technically difficult to implement and the results are difficult to interpret. Furthermore, the method requires metabolic modification of a reagent by the cells under study.

While it has been known for decades that excitable cells such as neurons and muscle cells undergo a rapid change in membrane potential when stimulated by a neurotransmitter, it has only recently become apparent that the membrane potential changes induced by physiologic stimuli are not limited to these specialized cells. By inserting microelectrodes into non-excitable cells, researchers have established that membrane potential changes are associated with their ligand-receptor interactions. In fact, it has been observed that the physiological events which occur in non-excitable cells subsequent to the binding of a ligand to a receptor can sometimes be duplicated by the addition to the cell suspension of agents which alter membrane potential in the same direction as occurs following ligand-receptor binding. Further research has developed new techniques for observing such changes. For example, a photometric method of measurement of changes in membrane potential in bulk cell suspensions have been described by P. J. Sims et al. (Biochemistry, Vol. 13, No. 16, 1974, page 3315). According to this method, the cell suspension is incubated with a cyanine or other dye which is positively charged, and capable of traversing the lipid layer of cell membranes. The ratio of intracellular to extracellular dye concentration changes with changes in cell membrane potential: as the cells become hyperpolarized, i.e., as the inside of the cells become more negative, more dye molecules enter the cells. In the Sims et al. method, these dyes are used in concentrations such that intracellular dye molecules form non-fluorescent aggragates, and the fluorescence of the free dye in the suspending medium is measured against the darker background of the cells. This fluorescence decreases with hyperpolarization of the cells. If only a small fraction of the cells in a suspension are sensitive to a given ligand, it is only this fraction which exhibits a change in membrane potential. In this case, the dye concentration in the medium will not change appreciably, and there will thus be no detectable change in the fluorescence of extracellular dye. In any event, this method cannot identify individual cells sensitive to the ligand.

W. N. Ross et al., in the Journal of Membrane Biology, Vol. 33, page 141 (1977) have described the use of merocyanine, oxonol, and cyanine dyes to measure rapid changes of membrane potential in excitable cells such as the giant axons of the squid nervous system. Linear changes in absorption, fluorescence, dichroism, and birefringence of the dyes were found to be associated with changes in membrane potential. The dyes most suitable for these measurements are merocyanines, which are negatively charged and thus do not readily permeate cell walls. Generally, these dyes do not stain cell membranes other than those of excitable nerve and muscle cells. Merocyanines have been observed to stain some non-excitable cell membranes, for example, immature or leukemic blood cells. However, such staining has been shown to occur independently of changes in cell membrane potential.

It is an object of the invention to provide a method of bioassay based on non-intrusive measurement of changes in membrane potential in individual cells. Another object is to provide a rapid, sensitive, and versatile method of bioassay directed to detecting the occurrence of and predicting the cellular response to ligand-receptor interactions. Yet another object is to detect ligand-receptor interactions in individual, non-excitable cells. Other objects are to provide novel techniques for screening potentially active drugs, for diagnosing the physiological malfunctioning of tissues, and for allergy and histocompatability testing. These and other objects and features of the invention will be apparent from the following description of the invention, some preferred embodiments thereof, and from the drawing.

SUMMARY OF THE INVENTION

The instant invention provides a rapid and sensitive, non-intrusive procedure for detecting cell membrane potential changes in non-excitable cells and for predicting the physiological response of non-excitable cells to modification by physical, pharmacological, biological, or chemical agents. In one form of the invention, the potential change is caused by ligand-receptor interaction. In another form, the change is non-specific such as occurs following injury to the cells.

In the former situation, the procedure is based on the observation that while the physiological response of a given cell to the binding of a specific ligand is often difficult or impossible to detect and often does not take place until hours or days after the interaction, a change in the ion flux across the membrane of the cell and resulting change in membrane potential occurs within a short time, typically under an hour. The approach of this embodiment of the invention involves determining a characteristic of individual cells that is representative of the membrane potential thereof, comparing the characteristic to a reference characteristic to detect differences in membrane potential, and using the observed changes as a marker indicative of the occurrence of a ligand-receptor interaction. In view of the large number of substances which exhibit activity as chemical messengers, the observed diversity of receptor sites on individual cells of a given cell population, and the diversity of physiological response of individual cells to specific ligands, it is an important feature of the invention that the response of individual cells (as opposed to bulk suspensions) to the exposure of ligands is detected.

Thus, the invention provides processes: (1) for determining the presence or absence of specific receptors for a given ligand on some or all of the cells in a cell population; (2) for determining the presence or absence in a mixture of substances of a specific ligand known to interact with members of a given cell population; (3) for studying the cumulative effects of combinations of ligands upon cells; (4) for comparing the effects of two or more ligands on a given cell population, and (5) for determining an indication of the physiological state of a cell population or subpopulation after exposure to a suspected toxin or other substance. Since several of the methods used to detect changes in membrane potential are non-destructive, the processes may be used in combination with cell sorting to produce cell populations rich in cells with desired receptor specificities while preserving cell viability.

In accordance with one form of the invention, non-excitable cells, typically in suspension, are contacted with a solution containing or suspected of containing one or more active ligands. The mixture is incubated under conditions in which complementary cell receptors and ligands bind to induce a physiological change in the cells on which binding occurs. Before, after, or during the incubation, a characteristic representative of the cell membrane potential of individual cells is detected. This detected characteristic is compared with a reference characteristic to detect changes in the membrane potentials and to obtain useful information.

The presence or absence of a given ligand in a solution may be determined by incubating the solution with a cell population including at least a subpopulation known to contain receptors for the ligand in question, detecting changes in the cell membrane potential in each of the cells making up the population, and comparing the distribution of membrane potential changes, if any, among the cells to the results, for example, of a reference characteristic comprising the results of the same assay run in parallel with the test sample containing an authentic sample of the ligand in question. An indication of the ligand concentration in the unknown can also be deduced by this technique.

The presence and frequency of cells which are reactive with a known ligand in a heterogeneous cell population can be determined in a similar manner by comparing changes in membrane potential among members of the population. By combining this technique with known methods of cell sorting, the researcher can obtain cell populations relatively homogeneous with respect to sensitivity to a specific ligand.

In another embodiment of the process, the physiological response of a non-excitable cell population to the exposure of two or more chemically distinct ligands can be predicted and compared by incubating solutions of respective ligands in plural cell samples, monitoring the direction, magnitude, and/or time course of changes in membrane potential in individual cells in respective cell samples, and then comparing measurements made in the respective samples. This technique can be used, for example, to screen synthetic substances suspected of being agonistic or antagonistic with respect to the natural ligand and to detect variation in cellular response of similar cells to functionally or structurally related ligands.

In another embodiment of the process, the cumulative effect of exposing two or more chemically distinct ligands to a population of non-excitable cells may be rapidly assayed by incubating the ligands and cell population, detecting changes in the cell membrane potential in individual cells, and comparing the detected potential changes to, for example, results run in parallel with the individual ligands, or a record of the predetermined cellular response to one or more of the individual ligands. In this way, drugs which behave as agonists or antagonist to natural ligands, and an indication of their optimum dose can be discovered.

In still another embodiment, the toxic effects of various agents upon cells is evaluated by measurement of membrane potential following exposure to such agents. The membrane potential of an injured cell must reach zero in the limit at which the membrane is breached. Lesser degrees of injury are detectable by a decrease in the magnitude of membrane potential compared to uninjured cells.

Several non-intrusive methods are contemplated for use in detecting and measuring the membrane potential in individual non-excitable cells. The presently preferred method involves the use of either membrane-permeant or membrane-bound dyes which associate with individual cells and have detectable optical characteristics which change in response to changes in membrane potential. Thus, ionic, cell membrane-permeant dyes, if incubated with the cells, rapidly equilibrate between opposite sides of cell membranes as a function of the membrane potential. A measurement indicative of the intracellular dye concentration is then made by photometric measurement of the fluorescence, absorption, or other optical property of the dye within the individual cell and of such other attributes of the individual cell (for example, cell volume) that must be known in order to determine the intracellular dye concentration. Where the cells being compared are homogeneous with respect to volume, the measurement representative of the amount of intracellular dye will be proportional to membrane potential. The photometric measurement may be accomplished by conventional microphotometry or by flow cytometry. When the optical property to be measured is fluorescence, the dye is preferably selected from among those characterized by increasing fluorescence quantum efficiency in solvents of decreasing polarity, and the concentration of dye in the medium is selected such as to discourage intracellular fluorescence inactivation by the formation of complexes of reduced fluorescence. Preferred fluorescent dyes are cationic cyanine dyes such as 3,3'-dihexyl-2,2'-oxacarbocyanine (diO-$C_6$-(3)).

Figure 1:
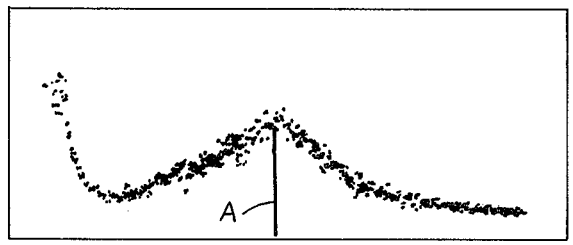
FIG. 1 is a graph of the distribution of cellular fluorescence intensity of a first aliquot of a human lymphocyte cell suspension incubated with $5 \times 10^{-8}$ M 3,3'-dihexyl-2,2' oxacarbocyanine (diO-$C_6$-(3)). In this and the following graphs, the vertical axis represents the number of cells with a particular intensity, and the horizontal axis represents fluorescence intensity.

All of the foregoing graphs were made with a flow cytometer (Cytofluorograf, Ortho Instruments) connected to a pulse height analyzer.

DESCRIPTION OF THE PREFERRED EMBODIMENT

The process of the invention involves the use of non-excitable cells, that is, cells other than from muscle and nerve tissue. The cells involved in the analysis in accordance with the procedure of the invention are isolated by conventional techniques and suspended in a medium capable of supporting normal cellular metabolism, e.g., a balanced, oxygenated, isotonic salt solution buffered to pH 7.2–7.6, and containing glucose or other nutrients, and approximately physiological concentrations of sodium, potassium, calcium, and magnesium ion. Preferably, the cells should be free of extraneous protein (albumin, etc.) and other substances having a strong affinity for dyes of the type used to detect membrane potential changes in the preferred detection technique disclosed below.

As required by the objectives of the test to be conducted, the cells may comprise a population relatively homogeneous with respect to physiological function (e.g. T lymphocytes), or with respect to ligand specificity (e.g., mast cells sensitive to IgE allergen complexes).

If required, the cells may be divided into plural aliquots so that several determinations of membrane potential can be made in parallel. The membrane potential of cells in each aliquot is then determined after exposure, for example, to a solution of different ligands, different concentrations of a single type of ligand, or a ligand-free solution, so that comparison can be made. The solution to which the cells are exposed, depending on the objectives of the test, may comprise an unknown suspected to contain a ligand specific for cells in the sample, an authentic sample of a known ligand of a known or unknown concentration, an impure ligand preparation, or a solution containing a substance suspected to be toxic to the cells or a subpopulation thereof.

In addition to detecting the occurrence of ligand-receptor binding, the technique of the invention is capable of ascertaining the following categories of information:

(1) the presence of a subpopulation of cells in the suspension having membrane surface receptors complementary to a specific ligand;

(2) the presence in a solution of a specific type of ligand capable of binding with receptors located on cells in the suspension or a subpopulation thereof;

(3) the cumulative effect of multiple ligands which interact with a given cell population;

(4) a comparison of the response of a cell population or subpopulation thereof to different types of ligands;

(5) the effect on cell viability of various concentrations of toxic substances; or (6) the stimulation of cell metabolism by various concentrations of nutrients, such as amino acids or sugars.

With respect to systems involving ligand-receptor interactions, the information is obtained by incubating the cells with the ligand solution for a sufficient amount of time and at a suitable temperature (e.g., the normal temperature of the cells in their natural environment) to allow the occurrence of ligand-receptor interactions and a resulting change in ion flux across the cell membranes. A characteristic representative of the membrane potential of each cell in the suspension or each cell in a representative aliquot of the suspension is then obtained, optionally at intervals so that a profile of potential change with time is obtained.

The measured characteristic is next compared to a reference characteristic to determine whether a ligand-receptor interaction has taken place, whether the direction, magnitude, or time course of the changes mimic or antagonize the changes induced in the cells on exposure to a known ligand, or whether the cumulative effect on membrane potential of the two or more ligands differs from that of a single ligand or a different mixture of ligands.

The nature of the reference characteristic will necessarily vary depending on the specific information sought. As noted above, it can comprise the results of one or more assays run in parallel with the test sample. Alternatively, it can take the form of a record of such an assay, such as a graph of the number of cells exhibiting a given potential versus the magnitude of the potential.

Ligands and their antagonists generally produce opposing effects on cell membrane potential. Accordingly, in research efforts directed to discovering substances capable of mimicking, blocking, or negating the effect of natural ligands on cells of a particular tissue, the direction, magnitude and/or time course of membrane potential changes in a cell sample of the tissue may be determined by multiple measurements after exposure of the cells to the natural ligand. Thereafter, various substances can be added to aliquots of the same cell suspension. By comparing the membrane potential changes induced in respective samples, the researcher can identify as worthy candidates for further research specific materials likely to have the desired physiological effect, and other compounds can be eliminated from consideration. Using the method of the invention, one can also determine such parameters as the concentration of antagonist needed to abolish the effect on membrane potential of a given cell type of a given concentration of agonist. Such measurements are useful in the evaluation of ligands and their antagonists as pharmacologic agents.

In some cases there exist several types of specific receptors for a given ligand. For example, the binding of ligand to receptors of one class of cells may result in hyperpolarization, while binding of the same ligand to receptors of a second class may result in depolarization. The method of the present invention can distinguish between these two types of interactions. Known cell sorting techniques, used in combination with the process disclosed herein, enable the isolation of cell lines having a desired receptor specificity from among heterogeneous populations. The use of the method in this context provides increased selectivity as compared to the customary method of sorting cells based on the binding of fluorescently tagged ligand because physiological effect as well as ligand binding may be incorporated into the selection criteria. Additional specificity may be obtained by the combination of direct measurement of binding of optically tagged ligand with detection of the change in membrane subsequent to ligand binding.

When the presence of a particular type of ligand in a solution, or the presence of cells having a particular ligand specificity is the information of interest, membrane potential can be read before and after mixing the ligand and cell suspension and the results compared. Respective representative aliquots of a cell suspension may be incubated with, for example, (1) a solution containing an unknown concentration of a given ligand, (2) a ligand-free solution, and (3) a solution containing a known concentration of the ligand. After incubation, an indication of the ligand concentration of the unknown may be obtained by comparing the membrane potentials of cells in the respective samples. Since the membrane potential of individual cells is detected, it is possible to identify a subpopulation of cells in the suspension with a selected ligand specificity.

The method may be used for the detection and quantitation of cellular immune responses by measurement of potential changes in lymphocytes, macrophages, or other cells of the immune system following exposure to substances such as antigens, antibodies, haptens, allergens, and components of complement. Since lymphocytes typically are a heterogenous population with respect to their reactivity to a given antigen, the fraction of cells responding to a given antigen provides a useful measure of cellular immune response. Alterations from the usual pattern of potential changes in responsive cells may indicate defects in the immune fraction. Similarly, the introduction of various allergens into plural samples of an individual's serum followed by incubation of the samples with cells involved in the excretion of histamine can be used as a non-intrusive means for detecting the sensitivity of an individual to various allergenic materials.

Since, in accordance with this invention, isolation and tagging of a specific ligand species is not required for the detection of substances capable of binding to cells with given receptor specificities, it is possible to use the method to assay ligand activity in impure preparation of ligand, and to follow and monitor ligand activity in various fractions of such impure preparations resulting from processes designed to purify or isolate the desired specific ligand.

The method may also be used as an aid in defining the chemical structure of surface receptors by demonstration of competition between various ligands of known specificity for binding sites on cell surfaces.

The toxic effects of various agents upon cells may be evaluated by sequential measurement of the membrane potentials of cells following exposure to such agents. It is known that tests for cell viability based on the admittance of normally impermeant dyes such as propidium iodide detect only those cells which are disintegrating. For many purposes, for example, the evaluation of drugs for cancer therapy, it is useful to determine whether a cell's future reproductive capacity is impaired, or whether a degree of damage short of disruption of the integrity of the cell membrane has occurred. The potential of an injured cell must reach zero in the limit at which the membrane is breached. Lesser degrees of injury are detectable by a decrease in the magnitude of the membrane potential compared to uninjured cells. The diminution or abolition of response to ligands and other substances which normally produce known changes in potential may also be detected by measurement of cell membrane potentials.

Since the distribution of permeant ionic compounds, e.g., drugs, across cell membranes is dependent on membrane potential, the method may be used to predict differences in drug uptake among different cell types. The method may also be used to provide a correction factor based on differences in dye uptake predicted on the basis of measured potential differences, which allow a variety of permeant ionic dyes, e.g., acridines, to be used as vital stains for the quantitation of various intracellular constituents, e.g., nucleic acids and glycosaminoglycans.

All of the foregoing procedures require a rapid, non-intrusive, and preferably non-destructive method of detecting the membrane potential or of obtaining a measurement proportional to the membrane potential of the $10^3$ to $10^6$ individual cells in a typical cell sample. The intrusion of microelectrodes into individual cells necessarily damages cell membranes and cannot realistically be used to detect membrane potential in each of the large number of cells in a cell suspension. The preferred detection method involves the use of cationic, cell membrane-permeant fluorescent dyes which, during incubation, partition between opposite sides of the cell membranes as a function of membrane potential. The intracellular concentration of dye or a parameter proportional to the concentration is then measured by optical techniques in a microphotometer or flow cytometer. On hyperpolarization, the affinity of the interior of the cell for the dye is increased; on depolarization, the affinity of the interior of the cell for the dye is decreased.

One class of dyes suitable for use in this technique are cationic cyanine dyes such as 3,3'-di-n-butyl-9-methyl and 3,3'-diethyl thiacarbocyanines, 3,3'-diethyl-2,2'-oxacarbocyanine, 2,3,3,1',3',3' hexamethylindocarbocyanine and dicarbocyanine, 3,3'-diethylthiadicarbocyanine, and preferably 3,3' dihexyloxacarbocyanine (diO-C$_6$-(3)). These dyes are available commercially from, for example, Accurate Chemical Company or Eastman Kodak.

It is advantageous that the selected dye exhibit an increased fluorescence quantum efficiency with decreasing polarity of the solvent and that the fluorescence and absorption maxima of the dye shift with changes in polarity in the solvent. These characteristics maximize the selectivity of detection of membrane associated dye within cells against the background of free dye in solution. It is also advantageous to use low enough concentrations of the selected fluorescent dye to minimize quenching of the fluorescence of intracellular dye due to formation of aggregates. In the case of the preferred cyanine dye (diO-C$_6$-(3)), concentrations at or below about $3 \times 10^{-7}$ M are preferred.

DiO-C$_6$-(3) is characterized by an increase in quantum efficiency of approximately 4.5 in n-octanol over aqueous solutions. Its absorption and emission maxima in n-octanol are approximately 10 nm higher than in aqueous solution. The amount of diO-C$_6$-(3) within individual cells is determined by measurement of fluorescence in the region of 504 nm following excitation at approximately 488 nm. Among the cyanine dyes in general, the desired solvent effects on quantum efficiency are more pronounced in carbocyanine dyes, which have the general formula R—(CH)$_3$—R', than in di- and tricarbocyanines with the general formula R—(CH)$_5$—R' and R—(CH)$_7$—R', respectively.

A microfluorometer may be used to measure fluorescence, but the measurement is accomplished most rapidly and precisely using a flow cytometer. The methodology of flow cytometry and cell sorting is described by P. K. Horan and L. L. Wheeless, Jr. in Science, Vol. 198, pages 149–157 (1977). Flow cytometers employing argon ion laser light sources are well suited for measurements according to the present invention. Such instruments are sold by several manufacturers, and are capable of automatically sorting cells on the basis of several criteria, e.g., fluorescent intensity, cell size, wavelength of fluorescence, and wavelength or intensity of absorption.

If the cell population under study is relatively homogeneous with regard to size and internal structure, and if the concentration of added dye and the number of cells suspended in the given volume of medium are kept relatively constant, the total amount of dye within a given cell, as measured by the intensity of the fluorescence from that cell, will be directly proportional to concentration and therefore to membrane potential. However, when mixed cell populations or varying concentrations of cells and/or dye are involved, additional measurements may be required. Since the intracellular concentration of dye is equal to the total amount of dye within the cell divided by the cell volume, a value proportional to the concentration of dye within a given cell may be obtained by measuring the total amount of dye as described above and dividing by a quantity proportional to cell volume. A measurement of the cell volume may be obtained concurrently with a reading of intracellular fluorescence in flow cytometers by electronic or optical measurement of cell size, e.g., the 3/2 power of cell cross-section, measured by scattering of light at angles near the axis of illumination. Advantageously, flow cytometric techniques allow this information to be gathered, electronically manipulated, and displayed automatically. The cytometer generates a signal representative of fluorescent intensity, a second signal representative of cell volume, and then determines the ratio of the signals. This ratio, which is proportional to membrane potential, can then be used as a cell sorting criterion and/or displayed.

Where the population of cells to be assayed is markedly heterogeneous with respect to cell volume or amount of dye binding material, a measurement proportional to the membrane potential may be obtained by using two dyes with different affinities for intracellular components. In this case, the intracellular fluorescence of both dyes can be measured. The increase or decrease in the ratio of intracellular dye contents is then proportional to the change in membrane potential, and is independent of cell volume and variations in the content of dye binding material among cells.

While established principles of chemistry allow the calculation of effects of variations in cell and dye concentrations in the medium upon the intracellular concentration of dyes, it is simpler in practice to adjust dilutions so that the concentrations of cells and of dye are approximately the same in all samples being compared.

Interference with photometric potential measurements may be caused by nonspecific staining of the cytoplasm of dead cells in which the integrity of the membrane has been lost. If a small amount of a normally impermeant dye such as ethidium bromide or propidium iodide is added to the medium, the nuclei of those cells with damaged membranes will be stained, while the dye will not enter viable cells. If the permeant dye used for potential measurements and the impermeant dye used to detect membrane damage have different optical properties, it is possible to make correlation measurements of one or more optical properties of each dye within each cell, and to eliminate damaged cells thus detected from further analysis. If the permeant dye used is the preferred diO-C$_6$-(3), and the impermeant dye is propidium iodide, the nuclei of damaged cells will emit red fluorescence in the region of 610 nm following excitation of 488 nm. This fluorescence is easily distinguishable by the observer or by photometric methods from the green fluorescence of diO-C$_6$-(3).

Photometric measurements of membrane potential may be combined with other measurements of the same cells to increase the analytical power of the method of the invention. For example, the response of cells in different phases of the cell cycle to a given ligand may be determined by simultaneous staining with diO-C$_6$-(3) and with a DNA fluorochrome such as Hoechst compound number 33342.

It is possible to measure optical properties other than fluorescence, e.g., absorption, to obtain an indication of the amount of dye within individual cells. In this case, it is preferred to use dyes which form intracellular aggregates with absorption maxima at wavelengths different from those of the free dye, and to use those dyes in sufficiently high concentrations so that a relatively large fraction exists within the cells in the form of aggregates. This maximizes the selectivity of detection of intracellular dye against the background of free dye in solution. Thiacarbocyanine dyes such as 3,3'-diethyl- and 3,3'-dipropylthiadicarbocyanine may exhibit this property under certain conditions. On binding to red blood cells, the former dye is known to exhibits a new absorption peak at approximately 590 nm, probably due to complexation of intracellular dye with hemoglobin. The absorption of cells at this wavelength may thus be measured to determine the amount of dye within the individual cells.

While photometric measurement of the uptake of cationic dyes is the preferred method of measuring changes in membrane potential, other techniques may be used. For example, even though the interior of non-excitable cells is negative with respect to the exterior, anionic dyes which have an affinity for solvents of decreasing polarity may be used. In this case, the dye will have an affinity for intracellular components despite its charge and will be absorbed within the cell. Its concentration will decrease on cell hyperpolarization and increase with depolarization.

It is also contemplated that non-photometric methods of detecting membrane potential may be employed. In this regard, changes in membrane potential can be determined in a known manner using radioactivity tagged cation such as carbon 14 or tritium labled quaternary ammonium or phosphonium salts. Details of this procedure are disclosed in *Methods of Enzymology*, H. R. Kaback, Academic Press, 1974 (page 698). See also, *Changes in Membrane Potential of Human Granulocytes Antecede the Metabolic Response to Surface Stimulation*, Proc. Natl. Acad. Sci., Vol. 75 No. 8, pp. 3818–3822, Aug. 1978 (H. M. Korchak et al.) and Biochemistry 14:25, 1975 (Schuldiner et al.). The uptake of these cations, like that of the cationic dyes, is a function of cellular membrane potential. Intracellular radioactivity can be assayed after washing the cells by spreading a monocellular layer of cells on a slide and exposing the slide to a photographic emulsion. Comparisons are made, for example, by subjecting a control sample to the same procedure and comparing the resulting autoradiographs. While this method of measuring cell membrane potential change is operative, it is not preferred since relatively long periods of time are necessary to expose the photographic emulsion used and the cell viability is not preserved.

Another non-photometric method of measuring membrane potential involves a modification of the techniques employed in conventional electronic cell counters. In these devices, individual cells suspended in saline are passed through an orifice interposed between a pair of electrodes which maintain a current in the suspending solution. The passage of a cell through the orifice varies the conductivity of the solution, resulting in a detectable voltage pulse. The height of the pulse is indicative of cell volume. Since the membranes of cells with different membrane potential typically have different ionic conductivities, signals containing information indicative of variations in the ion conductivity of the membrane of individual cells passing through the orifice can be obtained using alternating current. These may be used to compare the membrane potentials of individual cells, e.g. with the aid of a pulse height analyzer.

The invention will be further understood from the following nonlimiting examples.

EXAMPLE 1

Peripheral blood lymphocytes are obtained from donated blood and isolated by centrifugation over Hypaque-Ficoll density gradients. Rough estimates of the percentage of erythrocytes, monocytes, and granulocytes in the lymphocyte preparations are obtained by cytographic analysis of the red and green fluorescent signals of cells in aliquots stained with acridine orange. Cell counts are obtained and cell viability assessed by trypan blue exclusion.

Working solutions of diO-C$_6$-(3) may be prepared from $10^{-3}$ M or $5 \times 10^{-4}$ M stock solutions in ethanol. The concentrations of the working solutions should be adjusted to give a final dye concentration between $10^{-8}$ M and $5 \times 10^{-7}$ M when 10 ml of dye solution are added to 1.0 ml of cells diluted in medium 199 (Gibco).

Valinomycin (Sigma Chemical Company), a known ionophore capable of hyperpolarizing lymphocytes, is dissolved in ethanol at a concentration of 0.66 mg/ml. Gramicidin (ICN), a known ionophore capable of depolarizing lymphocytes, is also dissolved in ethanol (0.4 mg/ml). Phytohemagglutinin ("PHA", Difco, 2 mg/ml) and Concanavalin A ("Con-A", Sigma, 1 mg/ml) are dissolved in phosphate buffered saline. PHA and Con-A are lectins (ligands) known to be capable of binding to human peripheral lymphocytes.

Before any other experiments are done, the kinetics of dye uptake of cells are checked. 20 ml of dye solution is added to 2 ml of a diluted cell suspension containing $1-2 \times 10^{-5}$ cells/ml. The fluorescence of the cells is then measured in a flow cytometer. The peak of the fluorescence distribution is located and its position noted at one-minute intervals until it becomes stable. This typically occurs within 12 minutes when diO-C$_6$-(3') is used as the indicator dye.

Subsequent experiments are designed to keep constant the interval between addition of dye and lectin or ionophore, and measurement of fluorescence, which interval is preferably slightly longer than the observed equilibration time. A 15 to 20 minute time period is suitable for diO-C$_6$-(3) at the concentrations used here.

In one experiment, the fluorescence distributions of 5 aliquots of cell suspension were compared. At the time of dye addition (10 ul working solution of diO-C$_6$-(3)/ml cells), there is also added, respectively:
a. nothing (control sample)
b. PHA (10 ml working solution; final concentration 20 ug/ml)
c. Con A (10 ml working solution; final concentration 10 ug/ml)
d. Valinomycin (10 ml working solution; final concentration $6 \times 10^{-6}$ M) and
e. Gramicidin (10 ml working solution; final concentration $2 \times 10^{-5}$ M).

Samples are prepared at intervals of 3 to 6 minutes to allow time for cleaning of the flow system of the flow cytometer between samples. Fluorescence measurements of all samples are made using the same laser power and gain settings. Approximately equal numbers of cells are measured in each sample, and the fluorescence distributions from all samples are displayed on the same scale of a pulse height analyzer.

The results of the experiment are illustrated in FIGS. 1-5. These plots are produced when the fluorescent response of the cells is measured 15 minutes after addition of the dye and of the lectins or ionophores. DiO-C$_6$-(3) is used at a final concentration of $5 \times 10^{-8}$ M. Referring to FIG. 1, (control sample) it can be seen that there is a distribution of the intracellular concentration of the cyanine dye among cells of the population, as indicated by the distribution of intensity of the fluorescent response (x-axis). Thus, the observed membrane potential of individual members of the cell population varies prior to stimulation. However, membrane potentials are distributed about a peak indicated at line A, representing a large subpopulation of cells of some intermediate value of membrane potential.

Figure 2:
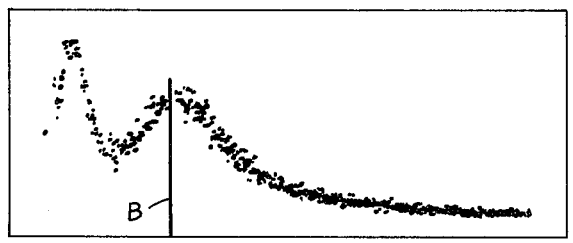
FIG. 2 is a graph of distribution of cellular fluorescence intensity of a second aliquot of the cell suspension incubated simultaneously with $2 \times 10^{-5}$ M gramicidin (depolarizing ionophore) and $5 \times 10^{-8}$ M diO-$C_6$-(3)
Figure 3:
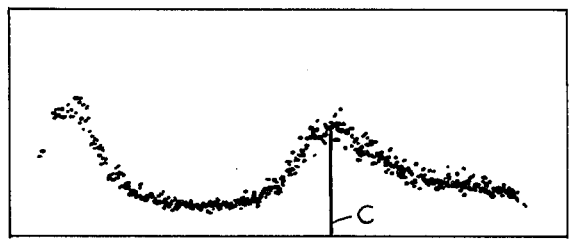
FIG. 3 is a graph of distribution of cellular fluorescence intensity of a third aliquot of the cell suspension incubated simultaneously with $6 \times 10^{-6}$ M valinomycin (hyperpolariing ionophore) and $5 \times 10^{-8}$ M diO-$C_6$-(3)

Referring to FIG. 2, the effect of adding the depolarizing ionophore gramicidin is shown. As illustrated, the number of cells exhibiting a reduction in fluorescent intensity (induced by the depolarizing effect of the gramicidin) is significantly increased, and there is a shift of the peak to the point indicated at B. In contrast, the cells to which the hyperpolarizing ionophore valinomycin was added (FIG. 3), exhibited an increase in the frequency of cells of higher fluorescent intensity, indicated at C.

The fluorescence intensity distributions of the gramicidin and valinomycin treated samples, when compared to the control sample, give an indication of the variation of the fluorescent signals to be expected following maximum depolarization and hyperpolarization. This example demonstrates that the cationic cyanine dye collects in the intracellular volume of individual cells as a function of membrane potential.

EXAMPLE 2

Figure 4:
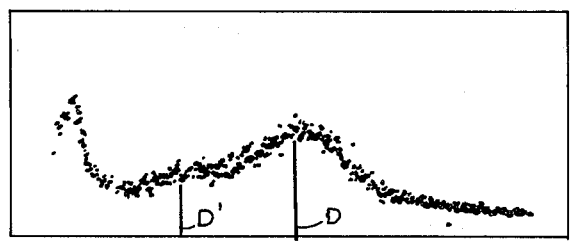
FIG. 4 is a graph of distribution of cellular fluorescence intensity of a fourth aliquot of the cell suspension incubated simultaneously with a 10 ug/ml solution of the ligand concanavalin A and $5 \times 10^{-8}$ M diO-$C_6$-(3)
Figure 5:
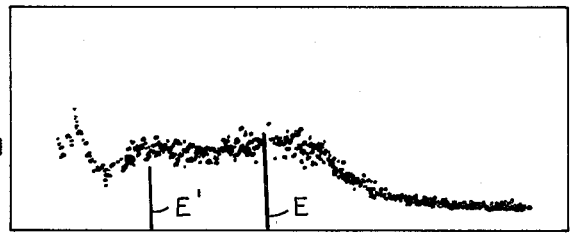
FIG. 5 is a graph of distribution of cellular fluorescence intensity of a fifth aliquot of the cell suspension incubated simultaneously with a 20 ug/ml solution of the ligand phytohemagglutinin and $5 \times 10^{-8}$ M diO-$C_6$-(3)

The effect of adding Con A to human lymphocytes is illustrated in FIG. 4. As shown, the lymphocyte suspension is heterogeneous with respect to its response to this lectin. It contains a subpopulation of cells which on binding with Con A is hyperpolarized, and another which is depolarized. Hyperpolarized cells exhibited an increase in fluorescent intensity as shown at D; depolarized cells exhibited a decrease in fluorescent intensity as shown by a faint but distinct peak at D'. The size of the hyperpolarized population is significantly greater than that of the depolarized population.

The addition of PHA to the cells results in a resolution of two groups of cells. The broad, bimodal distribution illustrated in FIG. 5 indicates that a subpopulation of the cells appear to depolarize on binding with PHA to a point such that the fluorescent response of individual cells decreased to a point indicated at E. A second subpopulation of cells exhibited a more drastic depolarization indicated by an even lower fluorescent response indicated at E'.

EXAMPLE 3

Stock solution of PHA and diO-C$_6$-(3) is added to a lymphocyte cell suspension prepared in accordance with Example 1. The flow cytometer is then set to separate cells having a fluorescent intensity corresponding to the intensities indicated at E and E', in FIG. 3. After a 15 minute incubation, the suspension is metered into the flow cytometer and resolved into three cell suspensions, two of which are rich in cells homogeneous with respect to their physiological response on binding with PHA.

EXAMPLE 4

Figure 6:
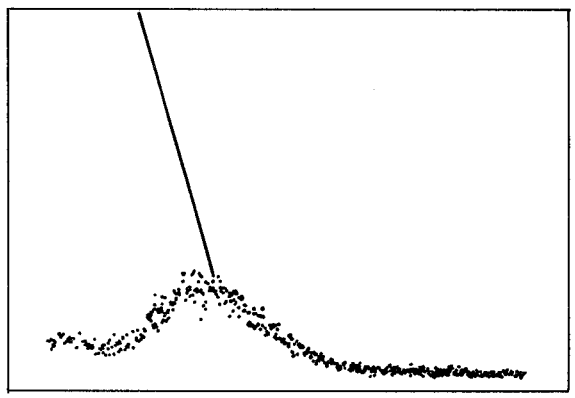
FIG. 6 is a graph of distribution of cellular fluorescence intensity of an aliquot of T lymphocytes equilibrated with $5 \times 10^{-8}$ M diO-$C_6$-(3)
Figure 7:
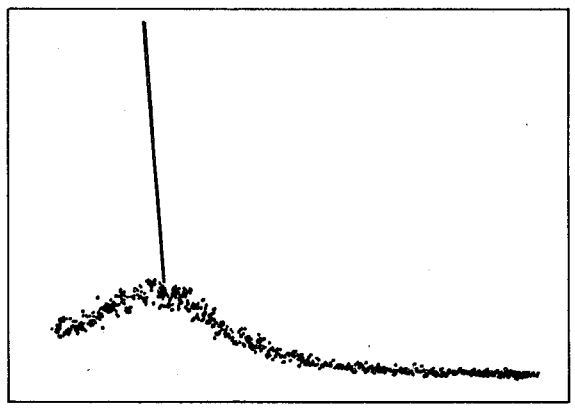
FIG. 7 is a graph of distribution of cellular fluorescence intensity of T lymphocyte suspension of FIG. 6 20 minutes after addition of phytohemagglutinin to provide a concentration of 20 ug/ml, showing the depolarizing effect of this lectin on a subpopulation of the T cells.
Figure 8:
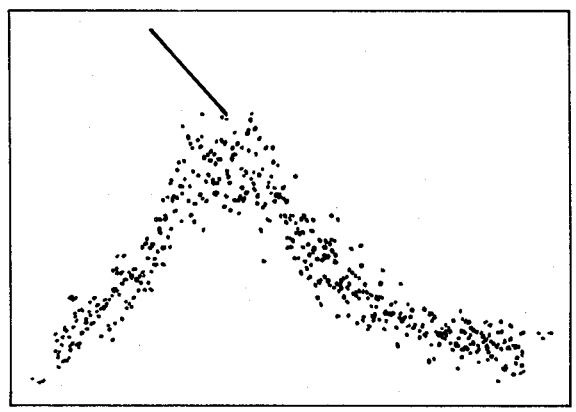
FIG. 8 is a graph of distribution of cellular fluorescence intensity of a B lymphocyte cell suspension equilibrated with $5 \times 10^{-8}$ M diO-$C_6$-(3)
Figure 9:
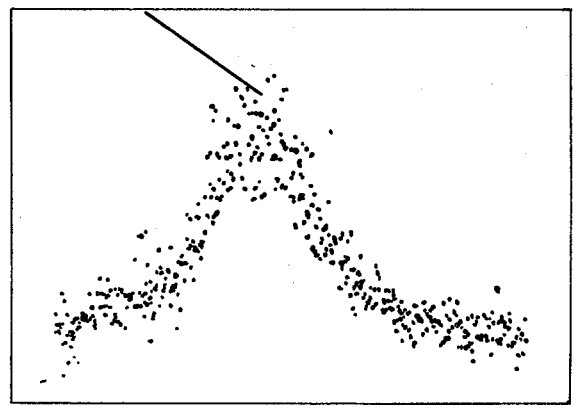
FIG. 9 is a graph showing the hyperpolarizing effect of phytohemagglutinin on the B cells suspension of FIG. 8 25 minutes after addition of phytohemagglutinin to a concentration of 20 ug/ml.

B enriched and T enriched populations of lymphocytes (about 85% pure) are obtained by rosetting and assayed for their sensitivity to PHA. FIG. 6 shows the fluorescent response distribution of the T cells in the suspension prior to the addition of the lectin; FIG. 7 shows the fluorescent response distribution of the same cell suspension 20 minutes after exposure to the PHA of the stock solution of Example 1. As illustrated, the addition of this lectin results in a uniform depolarization of T lymphocytes. In contrast, as shown in FIGS. 8 (control) and 9 (25 minutes after PHA addition) B cells undergo a uniform hyperpolarization as a result of PHA-receptor interactions. These results demonstrate that the process of the invention can be used to compare the physiological response of different cell types to a given ligand. It also demonstrates that different cell types may be distinguished on the basis of a physiological response to a ligand.

The invention may be embodied in other specific forms without departing from the spirit and scope thereof. Accordingly, other embodiments are within the following claims.

What is claimed is:

1. A bioassay method for one or more non-excitable cells, said method comprising the steps of:
   A. determining a characteristic of individual ones of said non-excitable cells representative of the membrane potential thereof by a non-intrusive method, and
   B. comparing said cell characteristic to a reference characteristic to detect differences in the membrane potential of said individual cells,
   wherein step A comprises the sub-steps of:
      (i) incubating said cells with a cell membrane-permeant ionic dye, and
      (ii) detecting an optical property of said individual cells, said optical property being representative of the intracellular dye level in the respective ones of said cells, and determining said cell characteristic from said optical property, and
   wherein step B comprises the step of:
      comparing said determined cell characteristic with said reference characteristic for said cells, and identifying differences in said determined cell characteristic with respect to said reference characteristic, said differences being representative of corresponding differences in cell membrane potential.

2. The method according to claim 1 wherein said detecting substep includes the step of detecting the intracellular concentration of said dye.

3. The method according to claim 2 comprising the further step of modifying said cells prior to sub-step (ii), whereby a change in cell membrane potential occurs prior to sub-step (ii).

4. The method according to claim 3 wherein said cell modification is physical.

5. The method according to claim 3 wherein said cell modification is pharmacological or chemical.

6. The method according to claim 3 wherein said cell modification is biological.

7. The method according to claim 3 wherein said modifying step precedes sub-step (i).

8. The method according to claim 3 wherein said modifying step succeeds sub-step (i).

9. The method according to claim 2 wherein said detecting sub-step (ii) comprises the sub-steps of:
   detecting the amount of said dye within said one cell,
   determining the volume of said one cell, and
   determining from said detected amount and said determined volume the concentration of said dye within said one cell.

10. The method according to claim 2 wherein said detecting substep (ii) comprises the sub-steps of:
    generating a first signal representative of the amount of said dye within said one cell,
    generating a second signal representative of the volume of one of said cells,
    generating a third signal representative of the ratio of said first and second signals, said third signal being representative of the concentration of said dye in said one cell.

11. The method according to claim 3 wherein said modification step comprises incubating said cells in a solution of ligands under conditions in which complementary cell receptors and said ligands bind.

12. The method according to claim 11 wherein said ligands include ligands selected from the group consisting of antigens, antibodies, haptens, allergens, and components of complement and said cells include cells of the immune system.

13. The method according to claim 11 wherein said ligands include one or more of the group of hormones, and natural or synthetic agonists or antagonists thereof.

14. The method according to claim 11 wherein said ligands include one or more of the group consisting of pharmacological agents, and natural or synthetic agonists or antogonists thereof.

15. The method according to claims 9 or 10 wherein said dye is a fluorescent dye and wherein said dye detecting step includes the step of:
    detecting fluorescence for one or more individual ones of said cells.

16. The method according to claims 9 or 10 wherein said dye is a fluorescent dye, and wherein said dye detecting step includes the step of:
    detecting the spectral shift of fluorescence for one or more individual ones of said cells.

17. The method according to claims 9 or 10 wherein said dye detecting step includes the step of:
    detecting optical absorption for one or more individual ones of said cells.

18. The method according to claims 9 or 10 wherein said dye detecting step includes the step of:
    detecting the spectral shift of optical absorption of one or more individual ones of said cells following aggregation of said dye.

19. A bioassay method for one or more non-excitable cells, said method comprising the steps of:
    A. determining a characteristic of individual ones of said non-excitable cells representative of the membrane potential thereof by a non-intrusive method, and
    B. comparing said cell characteristic to a reference characteristic to detect differences in the membrane potential of said individual cells,
    wherein step A includes the sub-steps of:
       (a) incubating the cells with a dye which associates with individual cells, and
       (b) detecting an optical characteristic of dye associated with the respective ones of said individual cells, said detected optical characteristics being indicative of the cell membrane potential of the respective ones of said individual cells.

20. The method of claim 1 or 2 or 19 wherein the reference characteristic comprises the results of an assay run in parallel with said cells.

21. The method of claim 19 wherein the reference characteristic is a value representative of a predetermined membrane potential and said comparison step determines the difference in magnitude between the detected potential and the potential corresponding to said reference characteristic.

22. The method of claim 19 wherein the reference characteristic is a value representative of a predetermined membrane potential and said comparison step determines the direction of change between the detected membrane potential and the potential corresponding to said reference characteristic.

23. The method of claim 19 comprising the step of incubating said cells with a substance which induces a change in the membrane potential thereof, wherein the reference characteristic comprises a plurality of measurements representative of a predetermined time course of membrane potential change in a reference cell, a plurality of optical characteristic determinations are made on said cells, and said comparison step determines the difference in the time course of a potential change between said cells and said reference cell.

24. The method of claim 19 comprising the additional step of incubating said cells in a solution of ligands under conditions in which complementary cell receptors and ligand bind, said ligands being selected from the group consisting of neurotransmitters, hormones, agonists and antagonists thereof, immune system proteins, and combinations thereof.

25. A bioassay method for one or more non-excitable cells, said method comprising the steps of:
  A. determining a characteristic of individual ones of said non-excitable cells representative of the membrane potential thereof by a non-intrusive method, and
  B. comparing said cell characteristic to a reference characteristic to detect differences in the membrane potential of said individual cells,
wherein step A comprises the sub-steps of:
  (i) incubating said cells with two or more cell membrane-permeant ionic dyes, and
  (ii) detecting an optical property of said individual cells, said optical property being representative of the ratio of the intracellular levels of said dyes in the respective ones of said cells, and determining said cell characteristic from said optical property, and
wherein step B comprises the step of:
  comparing said determined cell characteristic with said reference characteristic for said cells, and identifying differences in said determined cell characteristics with respect to said reference characteristic, said differences being representative of corresponding differences in cell membrane potential.

26. The method according to claim 25 wherein said detecting sub-step includes the step of detecting the intracellular concentrations of said dyes.

27. The method according to claim 26 comprising the further step of modifying said cells prior to sub-step (ii), whereby a change in cell membrane potential occurs prior to sub-step (ii).

28. The method according to claims 2 or 3 or 7 or 8 wherein said reference characteristic is a value representative of a predetermined concentration and said comparison step determines the difference in magnitude of said detected concentration and said predetermined concentration.

29. The method according to claims 2 or 3 or 7 or 8 wherein said reference characteristic is a value representative of a predetermined concentration and said comparison step determines the direction of change of the difference in magnitude of said detected concentration and said predetermined concentration.

30. The method according to claims 2 or 3 or 7 or 8 wherein said reference characteristic is a set of values representative of a predetermined concentration time course and said comparison step determines the differences in magnitude of said detected concentration and said predetemined concentration time course.

31. The method according to claim 28 including the further step of determining said reference characteristic by the steps of:
  performing steps A and B for one or more control cells and determining said predetermined value, said predetermined value being representative of the concentration of said dye in said control cells.

32. The method according to claim 29 including the further step of determining said reference characteristic by the steps of:
  performing steps A and B for one or more control cells and determining said predetermined value, said predetermined value being representative of the concentration of said dye in said control cells.

33. The method according to claim 30 including the further step of determining said reference characteristic by the steps of:
  performing steps A and B for one or more control cells and determining said set of values, said set of values being representative of the time course of concentration of said dye in said control cells.

34. The method of claim 1 or 2 or 26 wherein said dye is a fluorescent dye and wherein said optical property detected is fluorescence.

35. The method of claim 34 wherein said dye is selected from the group consisting of cationic fluorescent dyes characterized by increasing fluorescence quantum efficiency in solvents of decreasing polarity.

36. The method of claim 34 wherein the concentration of dye in the extracellular solution is such as to minimize intracellular fluorescence quenching by the formation of complexes of reduced fluorescence.

37. The method of claim 1 or 2 or 26 wherein the dye is selected from the group consisting of fluorescent, cationic cyanine dyes.

38. The method of claim 37 wherein the dye is a salt of 3,3'dihexyl-2,2' oxacarbocyanine.

39. The method of claim 1 or 2 or 26 wherein the optical property measured is absorption.

40. The method of claim 1 or 2 or 19, said method being directed to the detection of the presence of a ligand in a solution, said method comprising the additional step of: incubating one or more non-excitable cells known to contain a membrane bound receptor complementary to the ligand with said solution under conditions in which ligands and receptors bind, the presence of said ligand in said solution being indicated by a change in the membrane potential in the cells containing said receptor.

41. The method of claim 40 wherein the detected change in membrane potential is compared with a reference characteristic obtained by parallel assay of a solution containing a known concentration of said ligand to obtain a measure of the concentration of ligand in said solution.

42. The method of claim 1 or 2 or 19, said method being directed to the detection of the presence of cells having receptors complementary to a selected specific ligand in a plurality of cells heterogeneous with respect to ligand specificity, said method comprising the additional step of:
  incubating said plurality of cells with a solution containing said specific ligand under conditions in which complementary cell receptors and ligands bind, the presence of said cells having receptors complementary to said ligand being indicated by a change in the membrane potential of said cells.

43. The method of claim 42 comprising the further step of segregating cells exhibiting similar membrane potential changes to produce a cell population rich in cells sensitive to said selected ligand.

44. The method of claim 1 or 2 or 19, said method being directed to the detection of the presence in a cell population of cells having receptor sites complementary to a selected ligand but a different physiological response thereto, said method comprising the additional step of:

incubating said cell population with a solution containing said selected ligand to induce membrane potential changes in said cells of distinct magnitudes or directions.

45. The method of claim 44 comprising the further step of segregating cells exhibiting similar membrane potential changes to produce a cell population rich in cells sensitive to said selected ligand.

46. The method of claim 1 or 2 or 19, said method being directed to the comparison of the physiological response of a cell population exposed to plural chemically distinct ligands, said method comprising the additional steps of:

incubating samples of said cell population with respective ligands under conditions in which receptors and ligands bind; and monitoring changes in membrane potential in individual cells of respective cell samples.

47. The method of claim 1 or 2 or 19, said method being directed to the determination of the cumulative effect of exposing plural chemically distinct ligands to a population of cells, said process comprising the additional step of:

incubating the ligands and the cell population under conditions in which complementary cell receptors and ligands bind.

48. The method of claim 1 or 2 or 19, said method being directed to the determination of the viability of a cell population after exposure to a cell toxin, said method comprising the further step of:

incubating the cell population with said toxin.

49. The method of claim 46 wherein plural determinations of the membrane potential of cells in said population are made at intervals after exposure to said toxin.

50. The method of claim 1 or 2 or 19, said method being directed to the determination of the effect on a cell population after exposure to a cell nutrient, said method comprising the further step of:

incubating the cell population with said nutrient.

51. The method of claim 48 wherein plural determinations of the membrane potential of cells in said population are made at intervals after exposure to said nutrient.

* * * * *